US00PP26671P2

(12) United States Plant Patent
van der Knaap

(10) Patent No.: US PP26,671 P2
(45) Date of Patent: Apr. 26, 2016

(54) *SPATHIPHYLLUM* PLANT NAMED 'SPAMART'

(50) Latin Name: ***Spathiphyllum* Schott.**
Varietal Denomination: Spamart

(71) Applicant: Leonardus Johannes Maria van der Knaap, Naaldwijk (NL)

(72) Inventor: Leonardus Johannes Maria van der Knaap, Naaldwijk (NL)

(73) Assignee: Nubilus B.V., Naaldwijk (NL)

( * ) Notice: Subject to any disclaimer, the term of this patent is extended or adjusted under 35 U.S.C. 154(b) by 134 days.

(21) Appl. No.: 14/120,117

(22) Filed: Apr. 25, 2014

(51) Int. Cl.
*A01H 5/02* (2006.01)

(52) U.S. Cl.
USPC ..... Plt./364

(58) Field of Classification Search
USPC ..... Plt./364
See application file for complete search history.

*Primary Examiner* — Anne Grunberg
(74) *Attorney, Agent, or Firm* — C. A. Whealy

(57) ABSTRACT

A new and distinct cultivar of *Spathiphyllum* plant named 'Spamart', characterized by its upright, outwardly arching and uniform plant habit; freely clumping growth habit; bushy and dense plants; variegated leaves; freely flowering habit; white-colored spathes that are positioned above and between the foliar plane on strong and erect scapes; and good inflorescence longevity.

3 Drawing Sheets

Botanical designation: *Spathiphyllum* Schott.
Cultivar denomination: 'SPAMART'.

BACKGROUND OF THE INVENTION

The present invention relates to a new and distinct cultivar of *Spathiphyllum* plant, botanically known as *Spathiphyllum* Schott. and hereinafter referred to by the name 'Spamart'.

The new *Spathiphyllum* plant is a product of a controlled breeding program conducted by the Inventor in Naaldwijk, The Netherlands. The objective of the breeding program is to create new year-round flowering *Spathiphyllum* plants that have variegated leaves, numerous white-colored spathes and good postproduction longevity.

The new *Spathiphyllum* is a naturally-occurring whole plant mutation of *Spathiphyllum* Schott. 'Sparanke', disclosed in U.S. Plant Pat. No. 21,294. The new *Spathiphyllum* plant was discovered and selected by the Inventor as a single flowering plant within a population of plants of 'Sparanke' in a controlled greenhouse environment in Naaldwijk, The Netherlands in November, 2011.

Asexual reproduction of the new *Spathiphyllum* plant by tissue culture in a controlled environment in Naaldwijk, The Netherlands since December, 2011 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Spamart'. These characteristics in combination distinguish 'Spamart' as a new and distinct *Spathiphyllum* plant:

1. Upright, outwardly arching and uniform plant habit.
2. Freely clumping growth habit; bushy and dense plants.
3. Variegated leaves.
4. Freely flowering habit.
5. White-colored spathes that are positioned above and between the foliar plane on strong and erect scapes.
6. Good inflorescence longevity.

Plants of the new *Spathiphyllum* differ from plants of the mutation parent, 'Sparanke', in the following characteristics:

1. Plants of the new *Spathiphyllum* have variegated leaves whereas plants of 'Sparanke' have solid dark green-colored leaves.
2. Plants of the new *Spathiphyllum* are more freely flowering than plants of 'Sparanke'.
3. Plants of the new *Spathiphyllum* have shorter scapes than plants of 'Sparanke'.

Plants of the new *Spathiphyllum* can also be compared to plants of *Spathiphyllum* spp. 'Sparego', disclosed in U.S. Plant Pat. No. 11,457. In side-by-side comparisons conducted in Naaldwijk, The Netherlands, plants of the new *Spathiphyllum* differed from plants of 'Sparego' in the following characteristics:

1. Plants of the new *Spathiphyllum* were more freely clumping than plants of 'Sparego'.
2. Plants of the new *Spathiphyllum* had variegated leaves whereas plants of 'Sparego' had solid dark green-colored leaves.
3. Plants of the new *Spathiphyllum* had smaller spathes than plants of 'Sparego'.
4. Spathes of plants of the new *Spathiphyllum* were whiter in color than spathes of plants of 'Sparego'.

BRIEF DESCRIPTION OF THE PHOTOGRAPHS

The accompanying photographs illustrate the overall appearance of the new *Spathiphyllum* plant showing the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet is a side perspective view of a typical plant of 'Spamart' grown in a container.

The photograph on the second sheet is a close-up view of the upper and lower surfaces of typical leaves of 'Spamart'.

The photograph on the third sheet is a close-up view of a typical inflorescence of 'Spamart'.

DETAILED BOTANICAL DESCRIPTION

The aforementioned photographs and following observations and measurements describe plants grown during the winter in 17-cm containers in a glass-covered greenhouse in Naaldwijk, The Netherlands. Plants were grown under conditions and practices which approximate those generally used in commercial *Spathiphyllum* production. During the production of the plants, day temperatures ranged from about 19° C. to 24° C., night temperatures ranged from about 19° C. to 22° C. and light levels averaged 5,000 lux. Plants were 36 weeks old when the photographs and the detailed description were taken. In the following description, color references are made to The Royal Horticultural Society Colour Chart, 2007 Edition, except where general terms of ordinary dictionary significance are used.

Botanical classification: *Spathiphyllum* Schott. 'Spamart'.

Parentage: Naturally-occurring whole plant mutation of *Spathiphyllum* Schott. 'Sparanke', disclosed in U.S. Plant Pat. No. 21,294.

Propagation:

*Type*.—By tissue culture.

*Time to initiate roots*.—About eleven days at temperatures about 23° C.

*Time to produce a rooted young plant, summer*.—About 215 days at temperatures about 21° C.

*Time to produce a rooted young plant, winter*.—About 240 days at temperatures about 21° C.

*Root description*.—Medium in thickness, fibrous; white in color.

*Rooting habit*.—Moderately branching, medium density.

Plant description:

*Plant and growth habit*.—Upright and outwardly arching plant habit; overall plant shape, broadly obovate; moderately vigorous growth habit.

*Clumping habit*.—Freely clumping habit, bushy and dense growth habit; about eleven clumps develop per plant.

*Plant height, from soil level to top of leaf plane*.—About 40.5 cm.

*Plant height, from soil level to top of inflorescences*.—About 53.8 cm.

*Plant diameter or spread*.—About 53.6 cm.

*Leaf description*.—Arrangement: Alternate; simple. Length: About 25.6 cm. Width: About 5.2 cm. Shape: Narrowly elliptic. Apex: Narrowly apiculate. Base: Attenuate. Margin: Entire; slightly undulate. Texture, upper and lower surfaces: Smooth, glabrous; slightly leathery. Luster, upper and lower surfaces: Moderately glossy. Venation pattern: Pinnate. Color: Developing leaves, upper surface: Darker than between 141A and 147A; slightly dotted with close to 198D. Developing leaves, lower surface: Close to 137B. Fully expanded leaves, upper surface: Darker than between N137A and 139A; heavily dotted with close to 145D, 150D, 198D and 157B to 156C; venation, darker than N137AA. Fully expanded leaves, lower surface: Close to 137B to 137C; heavily dotted with close to 150D and 157A; venation, close to 144B. Petiole: Length (excluding geniculum): About 18 cm. Diameter, just below geniculum: About 4 mm. Diameter, at plant base: About 8 mm. Texture: Smooth, glabrous. Luster: Slightly glossy. Color, upper and lower surfaces: Close to 143A to 143B. Geniculum length: About 3.5 cm. Geniculum diameter: About 4 mm. Geniculum texture: Smooth, glabrous Geniculum luster: Slightly glossy. Geniculum color, upper and lower surfaces: Close to 138A. Wing length: About 15.6 cm. Wing diameter: About 8 mm. Wing color: Close to 143C.

Inflorescence description:

*Inflorescence arrangement and flowering habit*.—Cupped erect spathes with columnar spadices held above and between the foliar plane on strong and erect scapes; flowering structures arise from leaf axils; plants begin flowering about five months after planting; freely and continuous flowering year-round in The Netherlands; freely flowering habit, typically about twelve inflorescences develop per plant.

*Fragrance*.—Strong; sweet and pleasant.

*Inflorescence longevity*.—Inflorescences last about three weeks on the plant; inflorescences persistent.

*Spathe*.—Length: About 15 cm. Width: About 4.1 cm. Shape: Ovate to narrowly ovate. Apex: Apiculate; twisting. Base: Attenuate. Margin: Entire. Texture, upper and lower surfaces: Smooth, glabrous; slightly leathery. Luster, upper and lower surfaces: Glossy. Color: When developing, front surface: Close to 155A to 155B; at the apex, close to 141B. When developing, rear surface: Close to 155A; at the apex, close to 141B; main vein, close to 143B. Fully developed, front surface: Close to NN155C; at the apex, close to 143B; main vein slightly tinged with close to 143B; with development, color becoming closer to 144B. Fully developed, rear surface: Close to NN155C; main vein and at the apex, close to 144A.

*Spadix*.—Length: About 3.1 cm. Diameter: About 1.2 cm. Shape: Columnar, tapering towards the apex; apex, obtuse; base, obtuse; cross-section, rounded. Aspect: Mostly erect. Color: Immature: Between 150D and 157A. Mature: Close to 155A. Flowers: Quantity per spadix: Numerous, about 70. Shape: Rounded. Height: About 2.5 mm. Diameter: About 3.5 mm. Anther color: Close to 155A. Pollen amount: Scarce. Pollen color: Close to 155D. Stigma shape: Ovoid. Stigma color: Close to NN155A. Ovary color: Close to 155A.

*Scape*.—Length: About 35 cm. Diameter: About 4.5 mm. Strength: Strong. Aspect: Erect to about 20° from vertical. Color: Close to 143B; towards the base, close to 145C.

*Seeds and fruits*.—Seed and fruit development have not been observed on plants of the new *Spathiphyllum*.

Disease & pest resistance: Plants of the new *Spathiphyllum* have not been observed to be resistant to pathogens or pests common to *Spathiphyllum* plants.

Temperature tolerance: Plants of the new *Spathiphyllum* have been observed to be tolerant to temperatures ranging from about 15° C. to about 36° C.

It is claimed:

1. A new and distinct *Spathiphyllum* plant named 'Spamart' as illustrated and described.

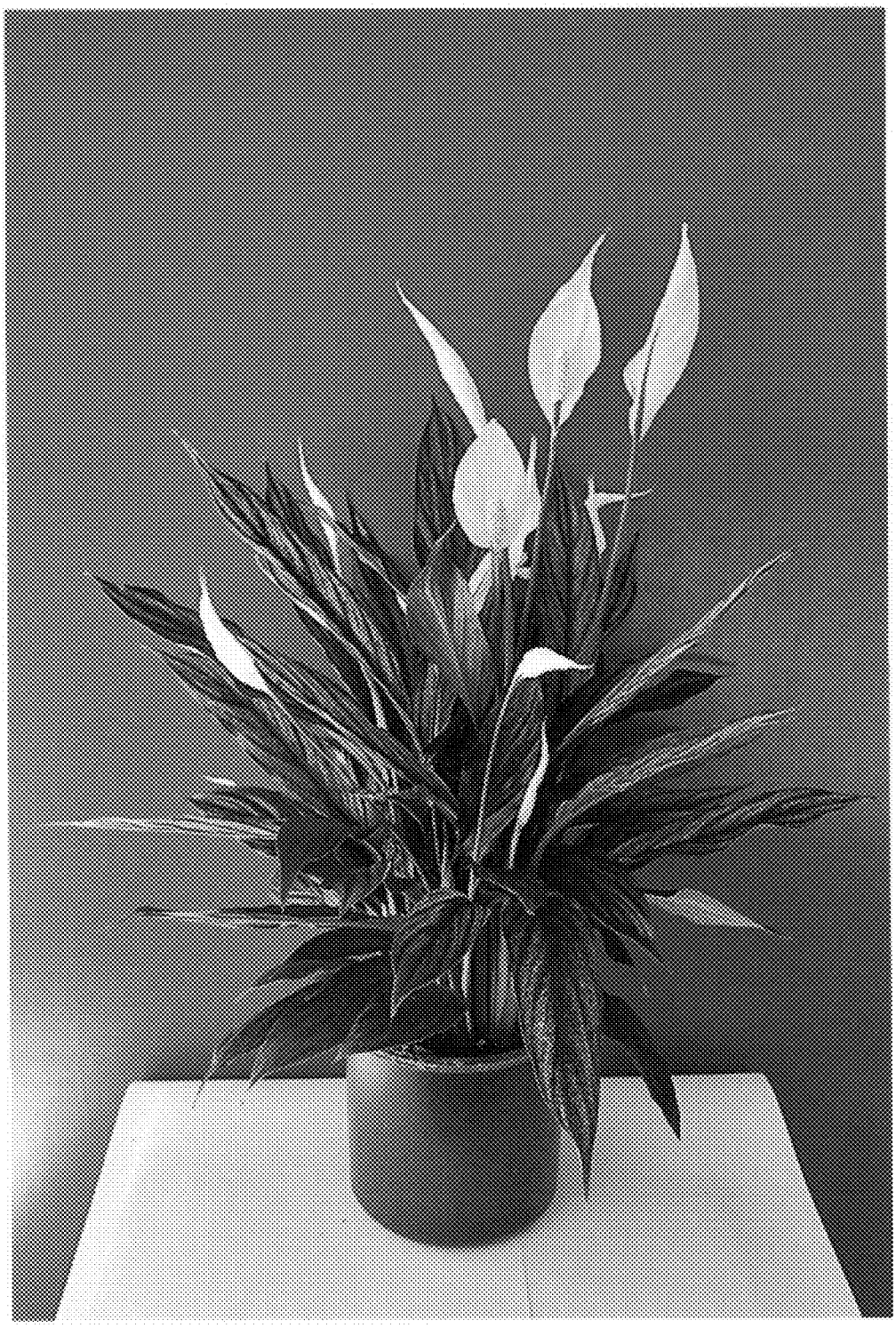

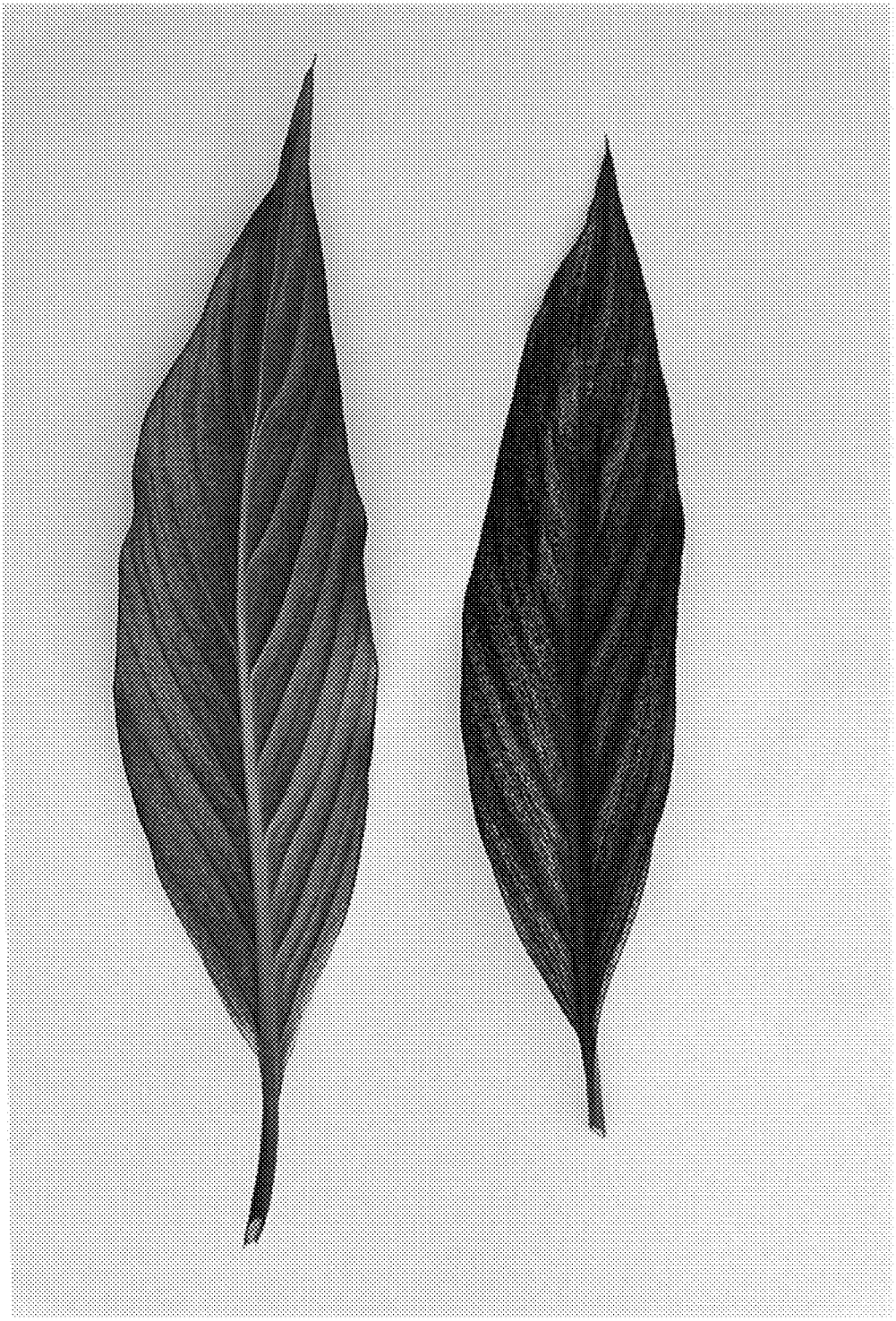

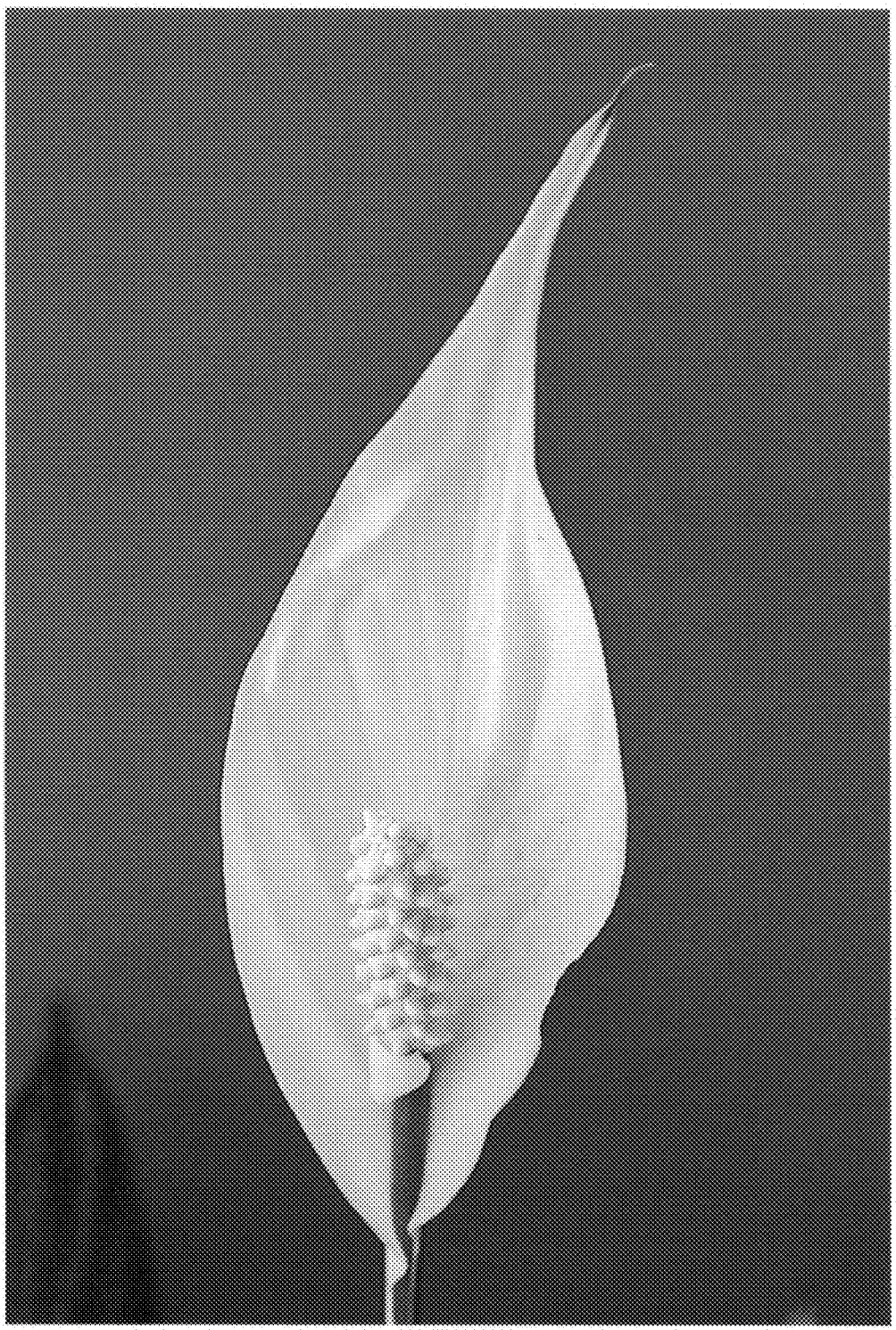

* * * * *